United States Patent [19]
Kritzinger et al.

[11] Patent Number: 5,752,967
[45] Date of Patent: May 19, 1998

[54] CORNEAL SURFACE MARKER AND MARKING METHOD FOR IMPROVING LASER CENTRATION

[76] Inventors: Michiel S. Kritzinger, 26 Wexford Avenue, Westcliff, Johannesburg, South Africa; Stephen A. Updegraff, 1635 N. Grand Vista Ct., Rapid City, S. Dak. 57701

[21] Appl. No.: 624,027

[22] Filed: Mar. 27, 1996

Related U.S. Application Data

[60] Provisional application No. 60/001,592, Jul. 27, 1995.

[63] Continuation-in-part of Ser. No. 561,541, Nov. 22, 1995, Pat. No. 5,697,945.

[51] Int. Cl.⁶ .................................................. A61F 9/00
[52] U.S. Cl. ..................... 606/166; 606/4; 606/5; 606/160; 606/161; 606/167
[58] Field of Search .................... 606/160, 161, 606/166, 167, 4, 5

[56] References Cited

U.S. PATENT DOCUMENTS

| | | | |
|---|---|---|---|
| 3,818,913 | 6/1974 | Wallach | 128/305 |
| 4,357,941 | 11/1982 | Golubkov et al. | 128/316 |
| 4,406,285 | 9/1983 | Villasenor et al. | 128/305 |
| 4,417,579 | 11/1983 | Soloviev et al. | 128/303 R |
| 4,515,157 | 5/1985 | Fedorov et al. | 128/303 R |
| 4,705,035 | 11/1987 | Givens | 128/303 R |
| 4,739,761 | 4/1988 | Grandon | 128/305 |
| 4,744,360 | 5/1988 | Bath | 128/303.1 |
| 4,963,142 | 10/1990 | Loertscher | 606/14 |
| 5,226,905 | 7/1993 | Hanna | 606/166 |
| 5,250,062 | 10/1993 | Hanna | 606/166 |
| 5,312,330 | 5/1994 | Klopotek | 604/49 |
| 5,314,439 | 5/1994 | Sungita | 606/166 |
| 5,342,378 | 8/1994 | Giraud et al. | 606/166 |
| 5,407,441 | 4/1995 | Greenbaum | 604/280 |
| 5,578,049 | 11/1996 | Feaster | 606/166 |

*Primary Examiner*—Michael Buiz
*Assistant Examiner*—Daphna Shai
*Attorney, Agent, or Firm*—Wood, Herron & Evans, L.L.P.

[57] ABSTRACT

A corneal surface marker is used to improve centration of surgical laser instrumention and repositioning of a corneal cap or flap in corneal surgery, particularly lamellar corneal surgery. The marker has inner and outer concentric rings with marking radials extending off the rings to provide adequate reference points for marking indicia to be placed on the corneal surface. The method involves positioning a patient's head with direct light thereby fixating and centering the laser instrumentation over the visual axis of the eye, preoperatively marking the corneal surface with a plurality of radial lines spaced about the visual axis, and aligning a reticule of a surgical laser instrument over the radial lines thereby permitting anatomic centration of the instrument over the visual axis for subsequent accurate surgical reshaping of the cornea.

14 Claims, 1 Drawing Sheet

CORNEAL SURFACE MARKER AND MARKING METHOD FOR IMPROVING LASER CENTRATION

RELATED APPLICATIONS

This application is a continuation-in-part of application Ser. No. 08/561,541, filed Nov. 22, 1995, now U.S. Pat. No. 5,697,945, which in turn is a continuation of Provisional Application Serial No. 60/001,592, filed Jul. 27, 1995. Both of these related applications are incorporated herein in their entireties by reference. This application is also related to applications Ser. Nos. 08/561,744, 08/562,257, and 08/562,253, all filed on Nov. 22, 1995, which are incorporated herein in their entireties by reference.

BACKGROUND OF THE INVENTION

Corneal surgery and particularly lamellar corneal surgery has undergone a steady evolution over the last 50 years. Advancements in the technology, such as automated keratomes and non-freeze, no-suture techniques have markedly improved safety and effectiveness. During the surface ablation craze of the late 80's, Dr. Gholam Peyman, known for his pioneering retina work, realized the utility of preserving all layers of the cornea while taking advantage of the extreme accuracy of the excimer laser (LASIK). He patented the method for LASIK years ago and studied this technique in his laboratory. He used a YAG laser due to the limited response and acceptance for this technique by the major excimer laser manufacturers. During the years of epikeratoplasty others such as Drs. Lee Nordan and Stephen Slade, as well as Dr. Casimir Swinger were learning and developing freeze myopic keratomileusis for high myopia. By the late 80's, Dr. Slade was one of a hand full of surgeons still performing this demanding technique. When Dr. Luis Ruiz introduced the automated keratome and the in situ non-freeze, no-suture technique to the lamellar bed, Dr. Slade embraced this and has since introduced this technique to thousands of surgeons worldwide. Although a significant advancement, even Dr. Luis Ruiz realized the relative imprecision of making a refractive pass with the keratome. He quickly learned to utilize the excimer laser to precisely reshape the cornea underneath the lamellar corneal flap. The precision achieved has been unparalleled, especially for the moderate to higher myopes.

Worldwide there have been many other surgeons that deserve credit for pursuing the combination of excimer laser with lamellar surgery, most notably Dr. Lucio Buratto of Milan, Italy, and Dr. Ioannis Pallikaris of Greece. The original Buratto technique, however, required cutting a very thick cap and ablating its under surface. Many of these lenticules required suturing. Thus, the technique required extreme surgical precision and, unfortunately, irregular astigmatism rates were quite high. Pallikaris' early work was done on animal models and provided the first histopathology of excimer laser to a lamellar bed. The early Summit excimer laser studies that evaluated the use of lamellar surgery were conducted by Brink et al.; however, there was a significant loss of best corrected visual acuity and a wide range of outcomes as new surgeons attempted to perform the original suture dependent Burrato technique.

As surgeons began doing lamellar corneal surgery, they became concerned about the potential for inducing irregular astigmatism as well as introducing debris such as epithelial inclusions in the stromal interface. Fortunately, with the introduction of the automated keratome and non-freeze, non-suture techniques, irregular astigmatism rates are reduced but still pose a great problem. Debris in the interface also continues to be a chronic problem. Many surgeons have resorted to never wearing gloves during lamellar surgery just for that reason. Although infections in lamellar surgery are quite low, infection percentages, however low, need to be reduced and preferably eliminated. At present, it is unclear whether or not wearing gloves during lamellar surgery is the standard of care. Thus, we need a way to perform lamellar surgery with gloves safely so as not to introduce debris into the interface.

There is a growing need to introduce lamellar surgery skills to surgeons new to this arena. Surgeons who have been performing ALK will be prepared to make an easy transition to LASIK. Many of the surgeons making the transition from PRK to LASIK appear totally consumed in what type of ablation to use in the bed, when in reality their primary concerns should be accurate centration of the laser instrumentation, safe keratectomy and repositioning the cap/flap so that there is the least likely chance for debris in the interface or irregular astigmatism. Indeed, during surface ablation, or LASIK, with the excimer laser, there can be a decentration of the ablation, or an "off-center" reshaping of the cornea relative to the patient's visual axis. This is a complication of excimer laser surgery that can contribute to glare, starburst, halos and loss of best corrected visual acuity.

There is a need to achieve accurate centration of the laser ablation without simply relying upon the patient's fixation during the laser procedure. During an ablation, sometimes the light that the patient is fixating upon is difficult to see or, simply, the patient becomes anxious as the laser procedure is underway, making it difficult to keep the eye position properly aligned. Small misalignments that a surgeon does not detect can lead to decentration and loss of visual acuity. If accurate centration can be achieved, then enhancement is more probable and predictability of the ablation for each surgeon will increase with experience.

Heretofore, improvements on techniques in this emerging surgical area and a variety of corneal surface markers which use more precise marking measures for marking the surface of the cornea during surgical procedures have been developed.

U.S. Pat. No. 4,357,941 discloses a tapered instrument for marking out the central optical zone of the cornea during surgical correction of myopia. The instrument has a circular end the diameter of which equals a preset diameter of the central optical zone of a particular patient. Further, a pointed rod-like sight is incorporated into the body of the instrument to aid in alignment. Thus, according to the disclosure, the instrument provides an accurate, clearly outlined central optical zone precluding any possibility of penetration therein when making incisions in the cornea thereby eliminating possible adverse effects. U.S. Pat. No. 4,705,035 also discloses an optical zone marker. This marker has a handle and a collar portion. The collar portion is circular and is adapted to impress an indentation into the cornea with normal hand pressure.

U.S. Pat. No. 4,406,285 discloses a template apparatus for use in manual radial keratotometry. The template is fixed on the eye by suction cups and provides slits to guide the surgical blades when altering the cornea during surgery. As shown in FIGS. 5 through 8, the slits can be in various configurations depending on the particular problem to be corrected.

Both U.S. Pat. No. 4,417,579 and U.S. Pat. No. 4,515,157 disclose corneal incision markers. The markers employ marking edges at one end of a bush which can be aligned in various arrangements. In use, a sufficient amount of force applied by the hand to the devices causes elastic non-destructive deformation of the cornea to mark where the incisions are to be made.

U.S. Pat. No. 4,739,761 discloses a cornea marker that is hand held. The marker has a blade assembly visibly protruding from beneath a radial dial guide allowing rotation of the assembly to selected alignments. The selected alignments aid in correct placement for the particular procedure to be employed.

U.S. Pat. No. 5,226,905 and U.S. Pat. No. 5,250,062 disclose similar instruments for surgery of the cornea. Both instruments are tubular and have annular bottom surfaces which are substantially spherical and are applied to the sclera of the eye of the patient just prior to the surgical procedure. In particular, FIG. 4 of the '905 patent illustrates the design of the annular bottom surface which is concave and has radial ribs for marking the surface of the cornea.

U.S. Pat. No. 5,314,439 also describes a tubular element for marking the cornea. The device provides marks on a recipient cornea bed of a corneal transplant patient. The tubular element, which has a spring to retract an inner tube relative to an outer tube, utilizes marking blades spaced circumferentially from each other in various configurations depending on the desired cutout section.

U.S. Pat. No. 5,342,378 discloses a sectioning device for lamellar surgery. FIG. 13 illustrates the marking indicia used in the device. Particular reference is made in the disclosure to an applanator which has these marking indicia on its interior surface. These indicia marked on the interior surface aid in centering the applanator. Furthermore, the use of concentric circles or rings of certain diameters to aid in the centering process is disclosed. According to the disclosure, the inner circle or ring has a diameter that varies from 3.6 mm to 6.5 mm. The outer circle or ring has a diameter of 7.25 mm. The crosshair inside the inner concentric ring aid in centering the ring and, in particular, aid in re-centering the ring for the proposed second cut. Indeed, the disclosure states that astigmatism can occur if the inner concentric ring is not centered for the proposed second cut.

Notwithstanding the above and other developments in lamellar or ophthalmologic surgery to date, however, new and more reliable techniques and instrumentation are needed to positively impact all lamellar surgeons who have grappled with decentration of surgical instrumentation, sight-threatening irregular astigmatism and debris in the interface.

SUMMARY OF THE INVENTION

The present invention is directed to an improvement in instrumentation and surgical technique for improving anatomic centration in corneal laser surgery. More particularly, this invention relates to a corneal surface marker and marking method for use during corneal surgery to improve centration of surgical laser instrumentation over the visual axis of the eye prior to laser ablation.

The corneal surface marker of the present invention comprises a marking surface having a plurality of radial markers for marking radial lines on the corneal surface which identify the visual axis of the eye thereby permitting accurate anatomic centration over the eye by alignment of the radial lines with a reticule of surgical laser instrumentation. The marker preferably has a stem or handle suitable for holding by hand and the marking surface has two concentric rings ensuring centration of the marker and subsequent centration of other instrumentation. Most preferably, there are four broad marking radials extending off of the inner ring and beyond the outer ring which provide adequate reference points for marking pharmacologically safe indicia on the corneal surface. The radial markers are circumferentially spaced approximately 90 degrees from each other and provide radial lines of sufficient width whereby a reticule crosshair can be visually superimposed over the radial lines for accurate alignment of the surgical laser instrument. Thus, the radial lines are wider than the lines of the crosshair which identifies the visual axis of the eye by alignment of the radial lines with the reticule crosshair of the laser instrument thereby permitting accurate anatomic centration. The marking radials aligned with a crosshair of a surgical instrument reticule also ensure centration of the marker and subsequent centration of other instrumentation.

Furthermore, the marker in its most preferred form has a pararadial which varies in width and extends off the inner ring and beyond the outer concentric ring ultimately permitting accurate anatomic repositioning of a free corneal cap or flap while preventing placement of the cap or flap with the epithelial surface down or, in other words, preventing the corneal cap from being placed upside down later in the surgical procedure. The area inside the inner concentric ring is devoid of markings preventing epithelial toxicity secondary to pharmacological dye near the visual axis of the eye. Moreover, the inner and outer concentric rings of the marker are circumferentially sized to outline the corneal surface and the optical zone of the corneal surface ensuring accurate centration of the marker for preoperatively marking the corneal surface with suitable indicia. In accordance with these outlines and in its most preferred form, the inner and outer concentric rings of the maker are approximately 5 mm and 10 mm in diameter, respectively. Also, the marking radials and pararadial are sufficiently circumferentially spaced around the concentric rings to provide adequate reference points for making indicia around the area of the corneal surface to be marked.

The most preferred method of marking the corneal surface according to the present invention comprises positioning a patient's head with direct light thereby fixating and centering the visual axis of the patient's eye. The above described marker is then placed over the area of the cornea to be marked and employed for preoperatively marking the corneal surface with suitable indicia, such as pharmacologically acceptable dyes, in accordance with the radials of the marker with a plurality of radial lines of sufficient width spaced about the visual axis. A reticule crosshair of a surgical laser instrument is aligned over the radial lines allowing for visual superimposition of the crosshair thereby permitting anatomic centration of the instrument over the visual axis for accurate surgical reshaping of the cornea.

These and other advantages of the present invention will become more apparent from the drawings and detailed description.

DETAILED DESCRIPTION OF THE INVENTION

Figure 1:
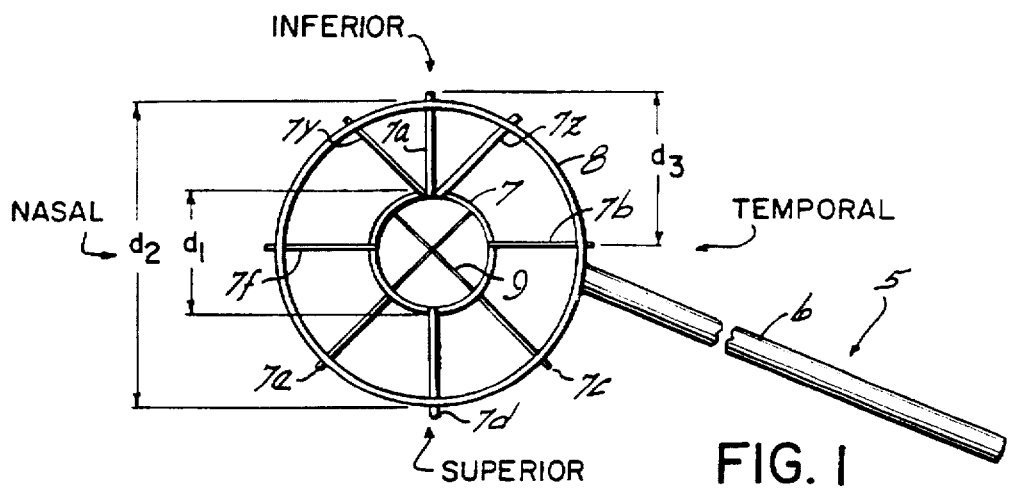
FIG. 1 illustrates a top view of the corneal surface marker of the present invention having two concentric rings with marking radials. Also illustrated are the nasal, inferior, temporal and superior regions surrounding the eye over which the surface marker is properly placed prior to marking the corneal surface.

Lamellar corneal surgery has undergone many changes in instrumentation and technique. The most recent advancement is excimer laser in situ keratomileusis or LASIK. This is a non-freeze, non-suture technique that incorporates the precise reshaping of the corneal stroma with the laser and the minimal wound healing/quick recovery of lamellar corneal surgery.

Prior to a lamellar dissection, a corneal surface marker of the present invention is used to outline the anatomical surface of the cornea for subsequent centration of laser surgical instrumentation for the forthcoming laser ablation procedure. Typically, once the lamellar dissection is made and it is appropriate to return the corneal cap/flap to its proper anatomic position, the corneal bed is irrigated with low flow tectonic fluid. The flap/cap is thereby returned. Fluid is aspirated from the fornices such that fluid flows from the bed (top of the dome of the eye) out and downward to the fornices. This first step removes debris and epithelium from the interface. Irrigation should start centrally and move peripherally. The second step requires an aspiration cannula to be placed gently on the edge of the keratectomy to prevent debris/epithelium from wicking back under the flap/cap. With a layer of irrigation fluid in the interface, the corneal flap/cap is then aligned pursuant to the preoperative surface marking of the present invention. If debris continues to be present or the cap is not aligned, the method is repeated and the surface markings are realigned.

The present invention and its advantages will be better understood from the following detailed stages of the surgical procedure aided by the use of the present invention incorporating references to the accompanying drawing figures. In the various figures, like reference characters are used to designate like parts.

A. Preoperative Stage of LASIK Corneal Surface Marking

1. Eye Prep

We recommend mild lid scrubs to the eyelid margins. Patients diagnosed with meibomianitis or blepharitis should be adequately treated prior to surgery. This may include a short term use of systemic Tetracycline to help reduce meibomian secretions prior to surgery. Be sure to confirm that the patient is not pregnant and is not planning to become pregnant over the next six months as this may affect the outcome of the surgery.

2. Irrigation of the Fornices

A thorough irrigation of the inferior fornices and glove with cool BSS should be conducted. As many have noticed for a long time during cataract surgery when meibomian secretions present as a layer in a pool of irrigating solution, a quick irrigation with the I&A with the head tilted will remove this oily film in a large sheet. This is what we believe is happening when the patient's head is tilted, and the lid scrubbed and the fornices are irrigated. Thus, meibomian secretions are not present during the keratectomy.

3. Eye Drops a. Pilocarpinte 2% is used before the marking ring over the constricted pupil.

b. Light Reflex Constriction

This can be a little more difficult for patients to fixate. It prevents pharmacologic decentration of the pupil and probably is the most accurate way to achieve centration over the entrance pupil.

B. Operative Stage of LASIK Corneal Surface Marking

1. Draping

This is one of the most important steps. Whatever drape you plan to use, it must retract the eyelashes out of the field and the drape should not restrict the speculum from opening fully so that adequate exposure of the globe can be obtained for suction. We presently use a 10-24 drape made by 3M to accomplish this.

2. Irrigation System

At present, we have been using the roller clamp on the IV bottle to control the flow of the BSS Plus through the irrigation cannula. This irrigation system is used to irrigate the globe and cornea prior to surgery.

3. LASIK Corneal Marker and Marking Method

The most recent advancement in corneal surgery is excimer laser in situ keratomileusis or LASIK. This is a non-freeze, non-suture technique that incorporates the precise reshaping of the corneal stroma with the laser and the minimal wound healing/quick recovery of lamellar corneal surgery. A major complication of LASIK corneal surgery which can be sight threatening or can cause unwanted visual deficiencies like glare or halos is decentration of the laser instrumentation in relation to the visual axis. To date, corneal surgeons have used subtle and often imperceptible visual cues such as light fixation to approximate the visual axis of the patient's eye. It is apparent that a slight decentration or disorientation of the laser instrumentation can result in irregular visual acuity.

Thus, with the above preoperative surgical procedures detailed and the dramatic problems of imprecise results of corneal surgery outlined, we propose an embodiment of a corneal surface marker of the present invention shown generally at 5 in FIG. 1 of the drawings. The corneal surface marker 5 improves centration of the surgical procedure and apparatus and aids in precisely repositioning a corneal cap or flap after the ablation stage of the surgical procedure.

Figure 2:
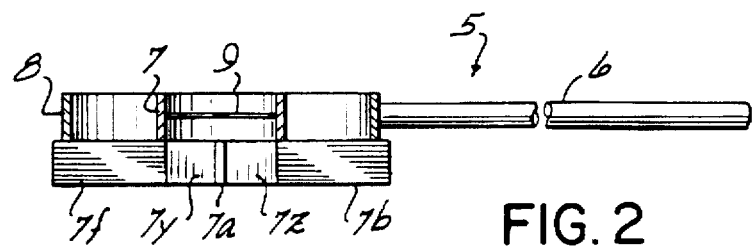
FIG. 2 is a cross-sectional side view of FIG. 1.
Figure 4:
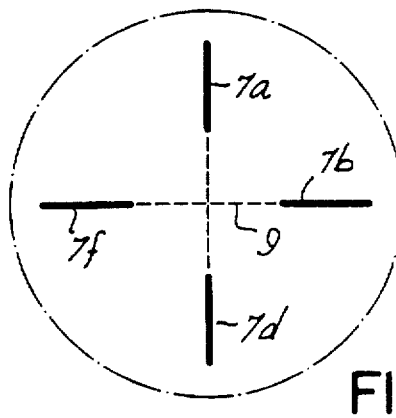
FIG. 4 is another illustration of the corneal radial marks directed by the present invention indicating the precise anatomical positioning of a reticule crosshair of a laser instrument over the visual axis of a human eye and proper repositioning of a corneal cap or flap resulting from a lamellar dissection.

In its most preferred embodiment, the Kritzinger-Updegraff (KU) LASIK marker 5 consists of a handle 6 (shown in FIG. 2) and two concentric rings, 7 and 8; ring 7 being 5 mm in diameter $d_1$ to aid centering with a crosshair of a laser instrument (shown at 9), and ring 8 being 10 mm to 10.5 mm in diameter $d_2$. The rings 7 and 8 of FIG. 1 may be formed of metal with radial blades $7a$–$7g$ and a pararadial blade $7z$ extending therefrom. The diameters of the rings are important in that they approximate the specific areas of the cornea to be covered and eventually worked. Further, radiating off the center ring 7 are seven radials, shown in the figures as $7a$, $7b$, $7c$, $7d$, $7e$, $7f$, fg and a pararadial, shown as $7z$, which extend approximately 6 mm from the center of the crosshair or at any length $d_3$ sufficient to cross and give adequate reference points past ring 8. These radial and pararadial markers vary in width as shown in FIG. 1 which permits accurate centration of surgical instrumentation and precise repositioning of the cap or flap edges after the keratectomy and ablation have been performed. Further, as shown in FIG. 1, marker 5 is properly placed over the eye in the position indicated and outlined by the surrounding regions of the eye. These regions are the nasal, temporal, inferior and superior. The width of the superior radial 7a and inferior radial 7b, superior radial 7d as well as nasal radial 7f, are at least two times thicker than the radials 7c, 7e, 7g and pararadial 7z. Further, in accordance with the marker and method of the present invention, the broader radials 7a, 7b, 7d and 7f are preferably located at 12:00, 3:00, 6:00 and 9:00 on the marker, extend off of the inner ring and provide adequate reference points for marking pharmacologically safe indicia on the corneal surface. With reference to FIG. 4, the radial markers are circumferentially spaced approximately 90 degrees from each other and provide radial lines of sufficient width (0.5 mm) whereby a reticule crosshair 9 can be visually aligned or superimposed over the radial lines for accurate alignment of the surgical instrument. Thus, the radial lines are wider than the lines of the crosshair which identifies the visual axis of the eye by alignment of the radial lines with the reticule crosshair 9 of the surgical laser instrument thereby permitting accurate anatomic centration. The marking radials 7a, 7b 7d and 7f aligned with a crosshair 9 of the surgical instrument reticule ensure centration of the marker and subsequent centration of other instrumentation.

The pararadial 7z in between the inferior and temporal regions is of a different width (0.25 mm) to ensure proper orientation of a free cap and prevent placement of a free cap upside down (epithelial surface down). The marker 5 was developed to permit a centered keratectomy which is dependent upon outer ring 8 mark of approximately 10 mm on which the surgeon centers a LASIK suction ring before the surgical incision is made. Additionally, the concentric rings 7 and 8 also ensure centration of the marker and subsequent centration of the LASIK suction ring or other appropriate instrumentation during the course of the surgical steps. The different widths of the pararadial and radials also permit accurate anatomic repositioning of the cap or flap after ablation microsurgery of the cornea is complete.

Figures 3A, 3B:
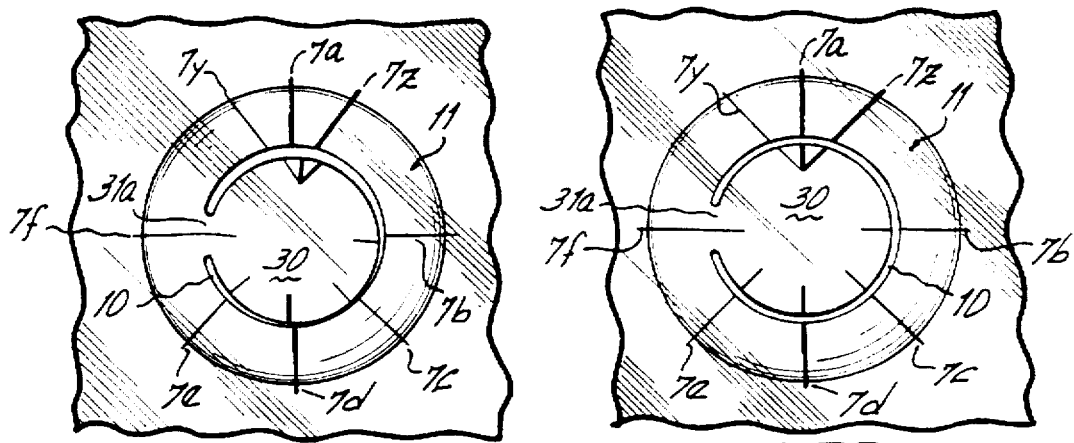
FIG. 3A is an illustration of a misaligned corneal cap post surgical procedure whereby the radial and pararadial marks directed by the present invention indicate the incorrect positioning of the corneal cap.
FIG. 3B is an illustration of a correctly aligned corneal cap post surgical procedure whereby the radial and pararadial marks directed by the present invention indicate the correct, accurate and precise anatomical repositioning of the corneal cap.

As shown in FIG. 3, the radiating marks extend beyond the incision ring created by the keratectomy and prevent micro-decentration seen when the surgeon uses an equally gapped gutter 10 in the cornea 11 as the cue for alignment. This latter imprecise method of alignment is thus rendered unnecessary.

When the marker 5 described in detail above is used with a marking dye and properly placed in position over the corneal surface and the marking radials and pararadials are aligned correctly, the pharmacologically safe dye is preoperatively placed as indicia on the corneal surface in the pattern outlined by the marker 5 so that the laser instrumentation may be properly aligned and the keratectomy and stromal reshaping by the surgeon may begin. Specifically, the method of marking the corneal surface to improve anatomic centration in corneal surgery comprises positioning a patient's head with direct light thereby fixating and centering said patient's visual axis of the eye, preoperatively marking the corneal surface in accordance with radial lines 7a, 7b, 7c, 7d, 7e, 7f, 7g and 7z spaced about the visual axis, and aligning a reticule 9 of a surgical laser instrument over said radial lines 7a, 7b, 7d and 7f thereby permitting anatomic centration of said instrument over the visual axis for subsequent accurate surgical reshaping of the cornea. Thereafter, the radial and pararadial markings are then aligned so that the free corneal cap or flap is accurately, anatomically repositioned reducing the possibility of irregular surgically-induced astigmatism. The correct anatomical alignment is illustrated in FIGS. 3 and 4 of the drawings.

4. Laser Centration a. Positioning the Patient's Head

The goal is to have the globe absolutely centered in the patient's socket as the patient fixates on the red fixation beam of the excimer laser device. An attempt should be made to position the patient's chin and forehead so that the globe is on a flat plane. It is important to make sure that the chin cannot move up or down and the head must be stable so that it cannot turn left or right. Once you have the globe centered within the orbit and looking straight ahead, use the joy stick of the X axis to bring the patient "dead" center in the crosshair that is in the optics of the right eye piece.

The KU marker 5 is positioned so that the superior and medial lateral marks of the crosshair of the reticule match with those of the marker ring 7, specifically 7a, 7b, 7d and 7f. Thus, after creating the mark, the crosshairs 9 can be superimposed upon the radial lines. If there is not absolute correspondence of the crosshair in the mark that is placed on the cornea, the surgeon is then responsible to make a "mental note" of this orientation when ablating the stromal bed and putting the flap back into position pursuant to the preoperative markings as outlined in the previous stage.

At this point, with the Keracor 116 laser, the red and green light must be superimposed prior to placing these marks or the crosshair will move away from the center of the pupil after these maneuvers have been performed.

b. Applying the Suction Ring

It is important to have the circular rings 7 and 8 of the KU marker 5 aligned concentrically with the LASIK suction ring. This ensures that the flap will properly be central to the pupil or the central optical zone.

c. Ablation

After the keratectomy is performed, the resulting flap or cap is folded back toward the nasal region. The peripheral markings of the KU marker are still visible. Thus, these are used as a visual cue to line up the crosshair of the redicule which correspond to the exact fixation prior to the keratectomy. It is very important not to move the joy stick of the excimer laser at this point to center the ablation. Rather, move the patient's head gently to achieve centration. Improper alignment of the patient's head does not mean the bed has moved but rather the patient's head has moved and thus must be oriented back to the position you had initially worked so hard to achieve. Thus, it is imperative that the joystick of the excimer laser is not altered from its original position.

It should be understood that the embodiments of the present invention shown and described in the specification are only preferred embodiments of the inventors who are skilled in the art and are not limiting in any way. Therefore, various changes, modifications or alterations to these embodiments may be made or resorted to without departing from the spirit of the invention and the scope of the following claims.

We claim:

1. An apparatus to improve anatomic centration in corneal laser surgery comprising:

a corneal surface marker having a plurality of radial markers for marking radial lines on the corneal surface which identify the visual axis of the eye thereby permitting accurate anatomic centration by alignment of said radial lines with a reticule of a surgical laser instrument, and a surgical laser instrument having a reticule for alignment with radial lines made by said marker on said corneal surface.

2. The apparatus of claim 1 wherein said marker has four radial markers circumferentially spaced.

3. The apparatus of claim 1 wherein said marker has a handle for manipulation of said marker.

4. The apparatus of claim 1 wherein said marker is sized to be placed over the human eye for centration of the radial markers.

5. The apparatus of claim 2 wherein said radial markers are circumferentially spaced for alignment with a reticule crosshair of the surgical laser instrument for accurate centration over the visual axis of the eye.

6. The apparatus of claim 5 wherein said radial markers provide radial lines of sufficient width whereby said reticule crosshair can be visually superimposed over said radial lines for accurate alignment of the surgical instrument.

7. The apparatus of claim 5 wherein said radial markers are spaced approximately 90 degrees from each other.

8. The apparatus of claim 7 wherein said radial lines are wider then the lines of said crosshair.

9. An apparatus to improve anatomic centration in corneal laser surgery comprising:

a corneal surface marker having a handle for manipulation of said marker and a marking surface having four radial markers for marking four radial lines on the corneal surface approximately 90 degrees from each other to Identify the visual axis of the eye for alignment of said radial lines with a reticule crosshair of a surgical laser instrument thereby permitting accurate anatomic centration, and a surgical laser instrument having a reticule crosshair for alignment with radial lines of said marker.

10. A method of marking the corneal surface to improve anatomic centration in corneal surgery comprising:

providing a corneal surface marker having a plurality of radial markers for marking radial lines on the corneal surface which identify the visual axis of the eye, preoperatively marking the corneal surface by using said marker with a plurality of radial lines spaced about the visual axis of the eye, and aligning a reticule of a surgical laser instrument over said radial lines thereby permitting anatomic centration of said instrument over the visual axis of the eye for accurate surgical reshaping of the cornea.

11. A method of marking the corneal surface according to claim 10 further comprising positioning a patient's head with direct light thereby fixating and centering said patient's visual axis.

12. A method of marking the corneal surface according to claim 10 by preoperatively marking the corneal surface with a pharmacologically safe dye.

13. A method of marking the corneal surface according to claim 10 wherein radial lines are of sufficient width and intersect the visual axis at approximately 90 degrees from each other.

14. A method of marking the corneal surface according to claim 10 wherein the reticule of said surgical laser instrumentation has a crosshair for alignment with said radial lines.

* * * * *